United States Patent [19]

Frysh

[11] Patent Number: 4,666,700
[45] Date of Patent: May 19, 1987

[54] DISCLOSING OF PLAQUE ON TEETH

[76] Inventor: Howard Frysh, P.O. Box 78519, Sandton, 2021, Transvaal, South Africa

[21] Appl. No.: 758,495

[22] Filed: Jul. 24, 1985

Related U.S. Application Data

[63] Continuation of Ser. No. 414,714, Sep. 3, 1982, abandoned.

[30] Foreign Application Priority Data

Jan. 22, 1982 [ZA]  South Africa ..................... 82/0437

[51] Int. Cl.$^4$ ........................... A61K 7/16; A61K 7/18
[52] U.S. Cl. ........................................ 424/7.1; 424/9; 424/48; 424/49; 424/52
[58] Field of Search ....................... 424/7.1, 9, 48, 49, 424/52

[56] References Cited

U.S. PATENT DOCUMENTS

| 3,903,252 | 9/1975 | Stearns et al. | 424/9 X |
| 4,202,878 | 5/1980 | Ritze | 424/49 |
| 4,302,439 | 11/1981 | Selwyn | 424/49 X |
| 4,348,378 | 9/1982 | Kosti | 424/49 X |
| 4,444,746 | 4/1984 | Harvey et al. | 424/49 |
| 4,459,277 | 7/1984 | Kosti | 424/7.1 |

Primary Examiner—Esther M. Kepplinger
Attorney, Agent, or Firm—Ladas & Parry

[57] ABSTRACT

An agent for use in disclosing dental plaque on a user's teeth comprises a non-toxic substantially water insoluble pigment. There is also disclosed compositions for use in disclosing dental plaque on a user's teeth comprising an amount of a non-toxic substantially water insoluble pigment sufficient to indicate the dental plaque and a non-toxic carrier therefor. The pigment is preferably a lake and the carrier may be a toothpaste base a tablet base, a liquid base or a chewing gum base.

9 Claims, No Drawings

DISCLOSING OF PLAQUE ON TEETH

This is a continuation of application Ser. No. 414,714 filed on Sept. 3, 1982, now abandoned.

FIELD OF THE INVENTION

This invention relates generally to the disclosing of plaque on teeth, and in particular to compositions suitable for use in such disclosure.

BACKGROUND TO THE INVENTION

It is well known that the object of cleaning one's teeth is to remove the layer of plaque that is deposited on them and which is the prime cause of tooth decay and gum diseases.

It is almost impossible, without assistance, to see whether one has removed all the plaque by brushing. To assist in proper brushing of the teeth disclosing agents are known which are placed in the mouth and which dye the plaque a colour which stands out against the clean tooth enamel. Brushing can then be continued until all the dyed areas have been removed.

Conventional disclosing agents are available in many forms, such as tablets, liquids or incorporated into a dentifrice as described in my South African Pat. No. 78/2334.

Although these disclosing agents are acknowledged as being effective in disclosing plaque it has been found very difficult to persuade people to use them on a regular basis. One of the main reasons for this is that all the existing disclosing agents use a water soluble dye to stain the plaque. A reasonably high dye concentration is required in order to produce the necessary colour contrast between plaque and enamel, and it is found that this dye concentration causes staining of the skin, tongue and mucosa. Although the staining is not serious and disappears in time, it is clearly a factor which holds people back from using disclosing agents on a regular basis.

SUMMARY OF THE INVENTION

According to the invention there is provided a composition for use in disclosing dental plaque on a user's teeth comprising an amount of a non-toxic substantially water insoluble pigment sufficient to indicate the dental plaque and a non-toxic carrier therefor.

According to another aspect of the invention there is provided a method of disclosing dental plaque on a user's teeth including the steps of placing a disclosing agent comprising a non-toxic substantially water insoluble pigment in the mouth, allowing the disclosing agent to disperse in the mouth and to contact the areas of dental plaque on the teeth, thereby colouring the areas of dental plaque, and observing the coloured areas.

Once the coloured areas have been observed, the teeth may be cleaned to remove the coloured areas and then the disclosing agent rinsed out of the mouth, with no staining of the skin, tongue or mucosa.

According to a further aspect of the invention, there is provided an agent for use in disclosing dental plaque on a user's teeth comprising a non-toxic substantially water insoluble pigment.

DESCRIPTION OF PREFERRED EMBODIMENTS

The crux of this invention is that a pigment is used as the disclosing agent. A pigment is a substance, usually in the form of a dry powder, that imparts colour to another substance. A pigment colours by dispersing the insoluble pigment particles amongst the substance to be coloured.

Included in the definition of pigments are lakes. A lake is an organic pigment produced by the interaction of an oil-soluble organic dye, a precipitant, and an absorptive inorganic substrate. Lakes are also insoluble in water.

Previously, the only disclosing agents which have been known and used have been dyes. There are several important differences between pigments (including lakes) and dyes, which make pigments more suitable as disclosing agents. The major difference between pigments and dyes is that dyes are soluble in water and in certain organic solvents such as propylene glycol and glycerine, whereas pigments are water insoluble and are also insoluble in many organic solvents. This difference leads to the second major difference which is that dyes are coloured chemical compounds which exhibit their colouring power or tinctorial strength when dissolved in a solvent. Dyes colour by being absorbed, in their dissolved state, on to the substance to be coloured. On the other hand, pigments colour by dispersion. The solid insoluble pigment particles are dispersed amongst the substance to be coloured and adhere thereto. This difference leads to the major advantage of pigments over dyes as disclosing agents. As pigments are water insoluble and are thus not absorbed, they may be removed by simple rinsing. Thus, there is no danger of pigments staining the skin, tongue or mucosa.

Dental plaque is a spongy mass with an uneven surface. Thus, it is thought that the pigment particles are preferentially trapped on the plaque surface to colour the plaque, and are not trapped on the smoother enamel surface. A contrast is thus produced between the plaque and the enamel to disclose the areas on the teeth where plaque remains. The plaque may then be removed by conventional means such as brushing, the use of dental floss etc.

Preferably, the pigment used as the disclosing agent is a lake. Preferred lakes are those comprising 1% to 40% by weight, preferably 10% to 30% by weight, of a water soluble dye on an alumina hydrate substrate. Particularly preferred lakes are those certified by the Color Certification Laboratory of the Food and Drug Aministration of the Health, Education and Welfare Department of the United States Government, for example, F.D. & C. Blue No. 1 Lake, F.D. & C. Blue No. 2 Lake, F.D. & C. Red No. 3 Lake, F.D. & C. Yellow No. 5 Lake and F.D. & C. Yellow No. 6 Lake.

The lake will generally have a particle size such that substantially all the particles will pass through a U.S.A. Standard Testing Sieve No. 325 (44 microns). Generally most of the particles will be less than 5 microns in size.

The lake should preferably have a low water bleed characteristic so that when the lake is placed in the mouth of a user, a minimum amount of dye will bleed out of the lake into the user's mouth.

The pigment may be combined with a suitable non-toxic carrier to form a composition suitable for oral administration for the disclosing of plaque on teeth.

Suitable compositions are for example, toothpastes, tablets, liquids and chewing gums.

When the composition is a toothpaste, it will generally comprise an amount of pigment sufficient to indicate the dental plaque, admixed with a toothpaste base. Generally the toothpaste will contain 5% to 50% by weight of pigment and 95% to 50% by weight of the toothpaste base. Preferably, the toothpaste will comprise 5% to 20% by weight of pigment and 95% to 80% by weight of the toothpaste base, more preferably 6% to 15% by weight of the pigment and 94% to 85% by weight of the toothpaste base. The toothpaste may also contain a minor amount, e.g. 0.1 to 1% by weight of a water soluble dye to potentiate the pigment.

The toothpaste base will generally comprise a major amount of an abrasive or polishing agent, and minor amounts of a preservative, a humectant, a sweetener, a foaming agent, a binding agent, a flavouring agent, optionally a fluoride compound, and water. The pigment, and optionally the dye, may be admixed with this base to give the toothpaste composition.

Other types of toothpaste bases, e.g. opague or gel toothpaste bases may be used.

An example of a suitable toothpaste composition will now be given:

|   | Constituent | Amount - % By Weight |
|---|---|---|
| A | Polishing agent<br>Dicalcium phosphate and carbonate | 54,65% |
| B | Preservative<br>Methyl paraben and propyl paraben | 0,90% |
| C | Humectant<br>Sorbitol and Glycerine | 19,40% |
| D | Sweetener<br>Sodium Cyclamate or Sodium Saccharin | 0,28% |
| E | Foaming Agent<br>Sodium lauryl sulphate | 1,75% |
| F | Flavouring Agent | 0,70% |
| G | Binding Agent<br>Carboxymethyl cellulose | 1,02% |
| H | Mono-fluorophosphate | 0,70% |
| I | Pigment<br>F.D. & C. Blue No. 2 Lake<br>(19-23% pure dye content) | 6,00% |
| J | Dye | 0,50% |
| K | Water | 14,10% |
|   |   | 100,00% |

Using the constituents given above, a toothpaste was made up as follows:

K was added to a mixing kettle. The constituents B, C, D and G were pre-mixed, then added to K, whilst heating and agitating the mixture until all the constituent G was dissolved and the mucilage was properly uniform. While continuing the mixing, A was slowly added, care being taken to avoid aeration of the mixture. Finally, in order, E, F, H, I and J were added and mixed in. The paste was then circulated through a pump of the Mono type to eliminate all lumps formed.

The use of this toothpaste for the disclosing of plaque on teeth will now be described. A user places a quantity of the toothpaste on his toothbrush and cleans his teeth in the normal manner. Thereafter he rinses his mouth out once only. At this stage the pigment provides the best disclosure of any plaque remaining on the teeth. The user then visually inspects the areas of plaque remaining and removes them either by further brushing or by the use of dental floss or the like. Once all the plaque has been removed, the user rinses his mouth out a few times until all the pigment has been washed out. There is no residual staining of the skin, tongue or mucosa.

When the composition is a tablet, it will generally comprise an amount of pigment sufficient to indicate the dental plaque, admixed with a tablet base. Generally, the tablet will contain 10 to 90% by weight of the pigment and 90 to 10% by weight of the tablet base. Preferably, the tablet will contain 10 to 25% by weight of the pigment and 90 to 75% by weight of the tablet base. The tablet base may comprise for example, dextrose, sucrose, mannitol, sorbitol or lactose.

When the composition is a liquid, it will generally comprise an amount of pigment sufficient to indicate the dental plaque, admixed with a liquid base to form a suspension or dispersion. The liquid base may comprise, for example, water or a syrup.

When the composition is a chewing gum it will generally comprise an amount of pigment sufficient to indicate the dental plaque, admixed with a gum base.

The composition which is a tablet, liquid or chewing gum may be used in substantially the same manner as the toothpaste composition. The composition is placed in the mouth of the user and the disclosing agent contained therein disperses and contacts the areas of dental plaque thereby colouring them. The coloured areas are observed by the eye and then the teeth are cleaned to remove the coloured areas. The disclosing agent may then be rinsed out of the mouth with no staining of the skin, tongue or mucosa. The teeth may be cleaned in any suitable manner, e.g. by brushing, the use of dental floss, toothpicks or the like.

I claim:

1. A method of disclosing the presence of dental plaque on a user's teeth comprising the steps of placing a disclosing agent comprising a non-toxic lake in the mouth of the user, allowing the disclosing agent to disperse in the mouth by brushing the disclosing agent on the teeth, or using the saliva and tongue to disperse it, and contacting the areas of dental plaque on the teeth, thereby colouring the areas of dental plaque by dispersion of lake and observing the coloured areas on the teeth.

2. A method according to claim 1 wherein after observing the colored areas on the teeth, the teeth are cleaned using a toothbrush, dental floss or toothpick to remove the colored areas and the disclosing agent is rinsed out of the mouth.

3. A method as in claim 2 wherein said lake comprises F D & C Blue No. 2 lake having a pure dye content of 19 to 23 percent.

4. A method as in claim 2 wherein said disclosing agent further comprises a material selected from the group consisting of preservatives, humectants, sweeteners, foaming agents, binding agents, flavoring agents, fluoride compounds, abrasives and mixtures thereof.

5. A method as in claim 1 wherein said disclosing agent further comprises a non-toxic carrier for the lake.

6. A method as in claim 5 wherein said disclosing agent further comprises a material selected from the group consisting of preservatives, humectants, sweeteners, foaming agents, binding agents, flavoring agents, fluoride compounds, abrasives and mixtures thereof.

7. A method as in claim 5 wherein said non-toxic carrier is a toothpaste base and the disclosing agent comprises the lake in the percent of 5 to 50 percent by weight, and the toothpaste base in the percent of 50–96 percent by weight.

8. A method as in claim 7 wherein said disclosing agent comprises the lake in the percent of 6 to 15 percent by weight and the toothpaste base in the percent of 84 to 90 percent by weight.

9. A method as in claim 5 wherein the non-toxic carrier comprises a material selected from the group consisting of a toothpaste base, a tablet, chewing gum and a liquid.

* * * * *